US010858390B2

(12) United States Patent
Collins et al.

(10) Patent No.: US 10,858,390 B2
(45) Date of Patent: Dec. 8, 2020

(54) USE OF EXCESS CARBODIIMIDE FOR PEPTIDE SYNTHESIS AT ELEVATED TEMPERATURES

(71) Applicant: CEM Corporation, Matthews, NC (US)

(72) Inventors: Jonathan M. Collins, Charlotte, NC (US); Sandeep K. Singh, Matthews, NC (US)

(73) Assignee: CEM Corporation, Matthews, NC (US)

(*) Notice: Subject to any disclaimer, the term of this patent is extended or adjusted under 35 U.S.C. 154(b) by 0 days.

(21) Appl. No.: 15/686,719

(22) Filed: Aug. 25, 2017

(65) Prior Publication Data

US 2018/0066013 A1 Mar. 8, 2018

Related U.S. Application Data

(60) Provisional application No. 62/382,949, filed on Sep. 2, 2016.

(51) Int. Cl.
| | | |
|---|---|---|
| C07K 1/08 | (2006.01) | |
| C07K 1/10 | (2006.01) | |
| C07K 1/107 | (2006.01) | |
| C07K 1/04 | (2006.01) | |
| C07C 267/00 | (2006.01) | |
| C07K 1/06 | (2006.01) | |

(52) U.S. Cl.
CPC .......... C07K 1/1075 (2013.01); C07C 267/00 (2013.01); C07K 1/04 (2013.01); C07K 1/045 (2013.01); C07K 1/061 (2013.01); C07K 1/082 (2013.01); C07K 1/084 (2013.01); C07K 1/10 (2013.01)

(58) Field of Classification Search
CPC ............. C07K 1/08; C07K 1/084; C07K 1/10
See application file for complete search history.

(56) References Cited

U.S. PATENT DOCUMENTS

| | | | |
|---|---|---|---|
| 5,486,476 A | 1/1996 | Burns | |
| 7,393,920 B2 | 7/2008 | Collins | |
| 7,550,560 B2 | 6/2009 | Collins | |
| 7,563,865 B2 | 7/2009 | Collins | |
| 7,582,728 B2 | 9/2009 | Collins | |
| 7,902,488 B2 | 3/2011 | Collins | |
| 7,939,628 B2 | 5/2011 | Collins | |
| 8,058,393 B2 | 11/2011 | Collins | |
| 8,153,761 B2 | 4/2012 | Collins | |
| 8,426,560 B2 | 4/2013 | Collins | |
| 8,846,862 B2 | 9/2014 | Collins | |
| 9,211,522 B2 | 12/2015 | Collins | |
| 2009/0149628 A1* | 6/2009 | King | C07K 14/605 530/303 |
| 2011/0318373 A1* | 12/2011 | Sasikumar | C07K 14/705 424/185.1 |
| 2012/0289683 A1* | 11/2012 | Schasteen | A23J 1/14 530/350 |
| 2013/0084278 A1* | 4/2013 | Amit | A61K 31/728 424/94.64 |
| 2015/0307550 A1* | 10/2015 | Nestor | C07K 7/06 514/21.8 |
| 2016/0031931 A1 | 2/2016 | Simon | |
| 2016/0176918 A1 | 6/2016 | Collins | |

FOREIGN PATENT DOCUMENTS

| | | |
|---|---|---|
| DE | 1937656 | 7/1969 |
| EP | 3037430 | 6/2016 |
| JP | H06279494 | 10/1994 |
| WO | 2015154031 | 10/2015 |

OTHER PUBLICATIONS

S. Nozaki, "Delay of coupling caused by excess additives," J. Pept. Sci., vol. 12, pp. 147-153, 2006.
M. Itoh, "Peptides. IV. Racemization Suppression by the Use of Ethyl-2-Hydroximino-2-cyanoacetate and Its Amide," Bull. Chem. Soc. Jpn., vol. 46, pp. 2219-2221, 1973.
R. Subirós-Funosas, "Oxyma: An Efficient Additive for Peptide Synthesis to Replace the Benzotriazole-Based HOBt and HOAt with a Lower Risk of Explosion," Chemistry, vol. 15, pp. 9394-9403, 2009.
J. Collins, K. Porter, S. Singh and G. Vanier, "High-Efficiency Solid Phase Peptide Synthesis (HE-SPPS)," Org. Lett., vol. 16, pp. 940-943, 2014.
L. Carpino, "The Diisopropylcarbodiimide/1-Hydroxy-7-azabenzotriazole System: Segment Coupling and Stepwise Peptide Assembly," Tetrahedron, vol. 55, pp. 6813-6830, 1999.
M. Beyermann, "Effect of tertiary amine on the carbodiimide-mediated peptide synthesis," Int. J. Peptide Protein Res., vol. 37, pp. 252-256, 1991.
R. B. Merrifield (1963) "Solid Phase Peptide Synthesis I, The Synthesis of a Tetrapeptide," J. Am. Chem. Soc. 85 (14), 2149-2154.
Chan and White, Fmoc solid phase peptide synthesis, a practical approach, Oxford University Press (2000).
S. Palasek, Z. Cox et al., "Limiting racemization and aspartimide formation in microwave-enhanced Fmoc solid phase peptide synthesis," J. Pept. Sci., vol. 13, pp. 143-148, 2007.
J. Collins, "Microwave-Enhanced Synthesis of Peptides, Proteins, and Peptidomimetics," in Microwaves in Organic Synthesis 3rd Ed., Weinheim, Germany, Wiley-VCH Verlag & Co. KGaA, 2013, pp. 897-960.
K. Wehrstedt, P. Wandrey and D. Heitkamp, "Explosive properties of 1-hydroxybenzotriazoles," J. Hazard Mater, vol. 126, pp. 1-7, 2005.
P. White, J. Collins and Z. Cox, "Comparative study of conventional and microwave assisted synthesis," in 19th American Peptide Symposium, San Diego, CA, 2005.

(Continued)

*Primary Examiner* — Jeffrey E. Russel
(74) *Attorney, Agent, or Firm* — Summa PLLC

(57) ABSTRACT

An improved method of coupling amino acids into peptides or peptidomimetics is disclosed in which the activation and coupling are carried out in the same vessel, in the presence of a carbodiimide in an amount greater than 1 equivalent as compared to the amino acid, in the presence of an activator additive, and at a temperature greater than 30° C.

5 Claims, 2 Drawing Sheets

Specification includes a Sequence Listing.

(56) References Cited

OTHER PUBLICATIONS

U.S. Patent Application for Coupling Method for Peptide Synthesis at Elevated Temperatures; U.S. Appl. No. 15/647,909, filed Jul. 12, 2017.
B. J. Egner, G. J. Langley and M. Bradley, J. Org. Chem., vol. 60, No. 9, pp. 2652-2653, 1995.
Wang et al., Gonadotropin-releasing hormone receptor-targeted paclitaxel-degarelix conjungate: synthesis and in vitro evaluation; J. Pept. Sci. 2015; 27: 569-576.
Standard textook Houben-Weyl: Methods of Organic Chemistry, vol. E 221: Synthesis of Peptides and Peptidomimetics, Georg Thieme Verlag 2002, p. 520.
Roy et al., "Dicyclohexylurea derivatives of amino acids as dye absorbent organogels and anion sensors," Org. Biomol. Chem., 2019, 17:3026-3039.
Standard textbook Stewart and Young: Solid Phase Peptide Synthesis, Pierce Chemical Company, 1984, pp. 31-33 and references on pp. 51 and 52.
Third Party Observation filed May 6, 2019 in counterpart Application No. EP17188963.7; 6 pages.

\* cited by examiner

SEQUENCE LISTING

```
<160> NUMBER OF SEQ ID NOS: 3

<210> SEQ ID NO 1
<211> LENGTH: 28
<212> TYPE: PRT
<213> ORGANISM: Artificial Sequence
<220> FEATURE:
<223> OTHER INFORMATION: Synthesized

<400> SEQUENCE: 1

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthesized

<400> SEQUENCE: 2

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25
```

```
<210> SEQ ID NO 3
<211> LENGTH: 76
<212> TYPE: PRT
<213> ORGANISM: Artificial Sequence
<220> FEATURE:
<223> OTHER INFORMATION: Synthesized

<400> SEQUENCE: 3

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

US 10,858,390 B2

USE OF EXCESS CARBODIIMIDE FOR PEPTIDE SYNTHESIS AT ELEVATED TEMPERATURES

REFERENCE TO SEQUENCE LISTING

This application incorporates by reference the sequence listing submitted on Sep. 14, 2018 in ASCII text file format in accordance with 37 CFR 1.824(a) titled "20180914_sequence_listing" created on Sep. 6, 2018 with a file size of 2 KB. The sequence listing is part of the specification and is herein incorporated by reference in its entirely. In accordance with 37 CFR 1.825(a), the sequence listing contains no new matter.

BACKGROUND

The present invention relates to peptide synthesis and in particular relates to solid phase peptide synthesis (SPPS).

A number of acronyms are used throughout the specification and claims. They are generally familiar to the skilled person. As used herein they have the following meanings:

EtOH: ethanol
HBTU: 2-(1H-benzotriazol-1-yl)-1,1,3,3-tetramethyluronium hexafluorophosphate.
HATU: 1-[Bis(dimethylamino)methylene]-1H-1,2,3-triazolo[4,5-b]pyridinium 3-oxide hexafluorophosphate.
HCTU: 1-[Bis(dimethylamino)methylen]-5-chlorobenzotriazolium 3-oxide hexafluorophosphate.
PyBOP: benzotriazol-1-yl-oxytripyrrolidinophosphonium hexafluorophosphate.
PyAOP: 7-Azabenzotriazol-1-yloxy)tripyrrolidinophosphonium hexafluorophosphate.
DIEA: Diisopropylethylamine.
NMM: N-Methylmorpholine.
Cys(Trt): Cysteine(trityl).
DMAP: 4-Dimethylaminopyridine.
NMP: N-Methyl-2-pyrrolidone.
TIS: triisopropylsilane.
DODt: 3,6-Dioxa-1,8-octane-dithiol.
MBHA: (4-methylbenzhydrylamine).

Probably the most commonly used and studied activation method for peptide synthesis is based on the use of carbodiimides. Their use in peptide synthesis dates back to 1955 where N,N'-dicyclohexylcarbodiimide (DCC) was used to facilitate amide bond formation. A carbodiimide contains two slightly basic nitrogen atoms which will react with the carboxylic acid of an amino acid derivative to form a highly reactive O-acylisourea compound as shown in FIG. 1. The formed O-acylisourea can then immediately react with an amine to form a peptide bond or be converted into other reactive species.

The high reactivity of O-acylisourea also promotes several other undesirable pathways that may or may not lead to peptide bond formation as also shown in FIG. 1. Conversion to the unreactive N-acylurea prevents coupling while epimerization of an activated chiral amino acid can occur through oxazolone formation. A highly reactive symmetrical anhydride can be formed by using excess amino acid compared to the carbodiimide. However, this approach undesirably consumes an additional amino acid equivalent.

A significant improvement for carbodiimide activation methods occurred with the incorporation of 1-hydroxybenzotriazole (HOBt) as an additive during carbodiimide activation. HOBt quickly converts the O-acylisourea into an OBt ester that is highly reactive and avoids undesirable N-acylisourea and oxazolone formation. It was later demonstrated that 1-Hydroxy-7-azabenzotriazole (HOAt) is an advantageous replacement for HOBt due to a neighboring group effect of the nitrogen at the 7-position [161]. Many other additives can be used in place of HOBt and HOAt such as 6-chloro-1-hydroxybenzotriazole (6-Cl-HOBt), ethyl 2-cyano-2-(hydroxyimino)acetate (Oxyma, OxymaPure, ECHA), and 1-hydroxy-2,5-pyrrolidinedione (NHS) to list several common examples.

Typically, 1 equivalent of additive is added compared to the amino acid and carbodiimide. A recent study suggested, however, that reduction of additives to less than 1 equivalent may be useful. (S. Nozaki, "Delay of coupling caused by excess additives," *J. Pept. Sci.*, vol. 12, pp. 147-153, 2006). The authors found that the acylation reaction could be hindered by salt formation between the amine and additive. The authors also found, however, that reducing additives to less than 1 equivalent slowed down the activation rate and slightly increased epimerization in segment couplings.

See FIG. 1 of Carbodiimide Based Activation.

N,N'-Diisopropylcarbodiimide (DIC) has largely replaced DCC as the preferred carbodiimide for peptide activation. DCC undesirably produces a urea soluble only in TFA which makes its use difficult for Fmoc chemistry. Additionally, DCC is a waxy solid that can be difficult to work with and has been reported to cause allergic reactions. Alternatively, DIC is advantageous due to the improved solubility of its generated urea in organic solvents, lower incidence of reported allergic reactions, and similar low cost as DCC. One of the most popular coupling methods still in use today is based on DIC/HOBt due to its low cost and side reactions while routinely providing effective couplings.

Recent analysis of benzotriazole based additives such as HOBt, HOAt, and 6-Cl-HOBt have led to their reclassification as class 1 explosives. This undesirable feature of benzotriazole additives has increased interest in developing suitable alternatives for the benzotriazole additives. One such alternative is Oxyma (ethyl 2-cyano-2-(hydroxyimino)acetate), first reported in 1973. (See, M. Itoh, "Peptides. IV. Racemization Suppression by the Use of Ethyl-2-Hydroximino-2-cyanoacetate and Its Amide," *Bull. Chem. Soc. Jpn.*, vol. 46, pp. 2219-2221, 1973). More recently, the explosive properties of Oxyma were tested by differential scanning calorimetry (DSC) as well as accelerating rate calorimetry (ARC) with favorable results as compared to HOBt. (R. Subirós-Funosas, "Oxyma: An Efficient Additive for Peptide Synthesis to Replace the Benzotriazole-Based HOBt and HOAt with a Lower Risk of Explosion," *Chemistry*, vol. 15, pp. 9394-9403, 2009).

Nevertheless, the use of carbodiimide based activation methods under room temperature synthesis conditions can lead to high levels of deletions due to both a relatively slow activation process and more acidic coupling environment. This has led to the more recent development of onium salt based activation methods which are more rapid. Onium salt based activation requires, however, the use of a base which first deprotonates the carboxylic acid thereby generating a carboxylate anion which reacts with the onium salt activator. Improved coupling has been demonstrated with many onium salts (HBTU, HATU, PyBOP, PyAOP, HCTU, among others) compared to carbodiimide based activation at room temperature conditions.

See FIG. 2 of Onium Salt Based Activation.

Starting in the early 2000's the use of heating during SPPS has been extensively applied as a method to improve amino acid coupling. Heating in peptide synthesis can be achieved by microwave irradiation or other known conventional heating methods, and has been used with both standard carbodiimide and onium salt coupling processes. Nevertheless, an elevated temperature during the coupling step presents several challenges for peptide synthesis. Using onium salt based activation methods, epimerization of cysteine derivatives is substantially increased at elevated temperatures based upon the presence of the base (typically DIEA, NMM). Additionally, increased δ-lactam formation of arginine during activation has been observed and leads to major arginine deletions in certain sequences.

Recently, Collins et al. showed that very rapid and efficient couplings could be performed by in-situ carbodiimide based couplings at 90° C. without the presence of any base. (J. Collins, K. Porter, S. Singh and G. Vanier, "High-Efficiency Solid Phase Peptide Synthesis (HE-SPPS)," *Org. Lett.*, vol. 16, pp. 940-943, 2014). This demonstrates that microwave irradiation is capable of accelerating both the slow activation process and subsequent acylation step; e.g., in 2 minutes at 90° C. The absence of base during the Collins et al coupling process advantageously avoided the hindered activation described by Carpino et al. and Beyermann et al, and provided a safer coupling environment from epimerization. In fact Collins et al showed that Fmoc-Cys(Trt)-OH could be coupled at 90° C. without an increase in epimerization compared to room temperature methods. (L. Carpino, "The Diisopropylcarbodiimide/1-Hydroxy-7-azabenzotriazole System: Segment Coupling and Stepwise Peptide Assembly," Tetrahedron, vol. 55, pp. 6813-6830, 1999; M. Beyermann, "Effect of tertiary amine on the carbodiimide-mediated peptide synthesis," *Int. J. Peptide Protein Res.*, vol. 37, pp. 252-256, 1991).

Nevertheless, the more acidic environment at higher temperatures required to drive the less reactive carbodiimide activation (compared to onium salts) will lead to premature cleavage of peptides attached to hyper-acid sensitive linkers (ex. 2-chlorotrityl). This can results in total loss of peptide from the resin and significantly limits the temperature that can be applied with this class of linkers. The use of hyper-acid sensitive linkers is important in certain peptide syntheses because they allow for peptide fragment condensation which allows for larger peptide sequences to be constructed. Hyper-acid linkers are also important for avoiding side reactions such as diketopiperazine formation, avoiding DMAP during resin loading, and avoiding beta-elimination of c-terminal cysteine residues connected to acid linkers.

Therefore, a peptide chemist faces limitations when applying elevated temperature to the coupling step in peptide synthesis with either carbodiimide or onium salt based activation methods.

It has been suggested that excess carbodiimide is reactive with amino groups and is undesirable for peptide bond formation which has led to avoidance in the use of excess carbodiimides. However, in rare cases the use of excess carbodiimide has been explored.

In one report, excess DIC/HOBt was used relative to the amino acid with undesirable capping of the amino group by excess carbodiimide reported through the observation of N-acylurea peptide formation. (B. J. Egner, G. J. Langley and M. Bradley, *J. Org. Chem.*, vol. 60, no. 9, pp. 2652-2653, 1995).

The use of excess carbodiimide has also been viewed as undesirable due to the difficult solvation properties of formed acylureas after coupling. This is a particular challenge with DCC whose urea is insoluble in many solvents thereby requiring the use of dichloromethane (DCM). This factor has largely led to its replacement with DIC whose urea is more soluble in DMF.

Very recently, an improved coupling method for SPPS was presented in U.S. Ser. No. 14/969,004, which demonstrated an improvement in coupling over both standard carbodiimide and onium salt based methods at elevated temperatures. This method is a modified carbodiimide activation strategy which features the use of a base. It was found that a strong base added at less than 1-equivalent compared to the amino acid, carbodiimide, and activator additive could be present during the entire activation and coupling process while both enhancing the overall coupling reaction and avoiding potential side reactions. Only a slight increase in epimerization was observed through the use of a limited amount of base.

Therefore, a need exists for a peptide synthesis scheme that can incorporate the advantages of elevated temperatures while avoiding these various disadvantages.

SUMMARY

An improved method of coupling amino acids into peptides or peptidomimetics is disclosed in which the activation and coupling are carried out in the same vessel, in the presence of a carbodiimide in an amount greater than 1 equivalent as compared to the amino acid, in the presence of an activator additive, and at a temperature greater than 30° C.

In some embodiments the carbodiimide is present in an amount greater than 1.5 equivalents as compared to the amino acid.

In some embodiments the method is limited to a total coupling time less than 10 minutes.

In some embodiments the carbodiimide is present in an amount greater than 1.5 equivalents as compared to the amino acid.

In some embodiments the method is limited to a total coupling time less than 10 minutes and carried out at a temperature greater than 30° C.

In some embodiments the method includes limiting the amount of carbodiimide present to between about 1.5 and 4 equivalents compared to the amino acid.

In some embodiments the method is limited to a total coupling time less than 10 minutes and carried out at a temperature greater than 70° C.

In some embodiments, the method is a solid phase peptide synthesis (SPPS) method.

In some embodiments at least one of the added acids is initially Fmoc-protected.

The foregoing and other objects and advantages of the invention and the manner in which the same are accomplished will become clearer based on the followed detailed description.

DETAILED DESCRIPTION

Figure 1:
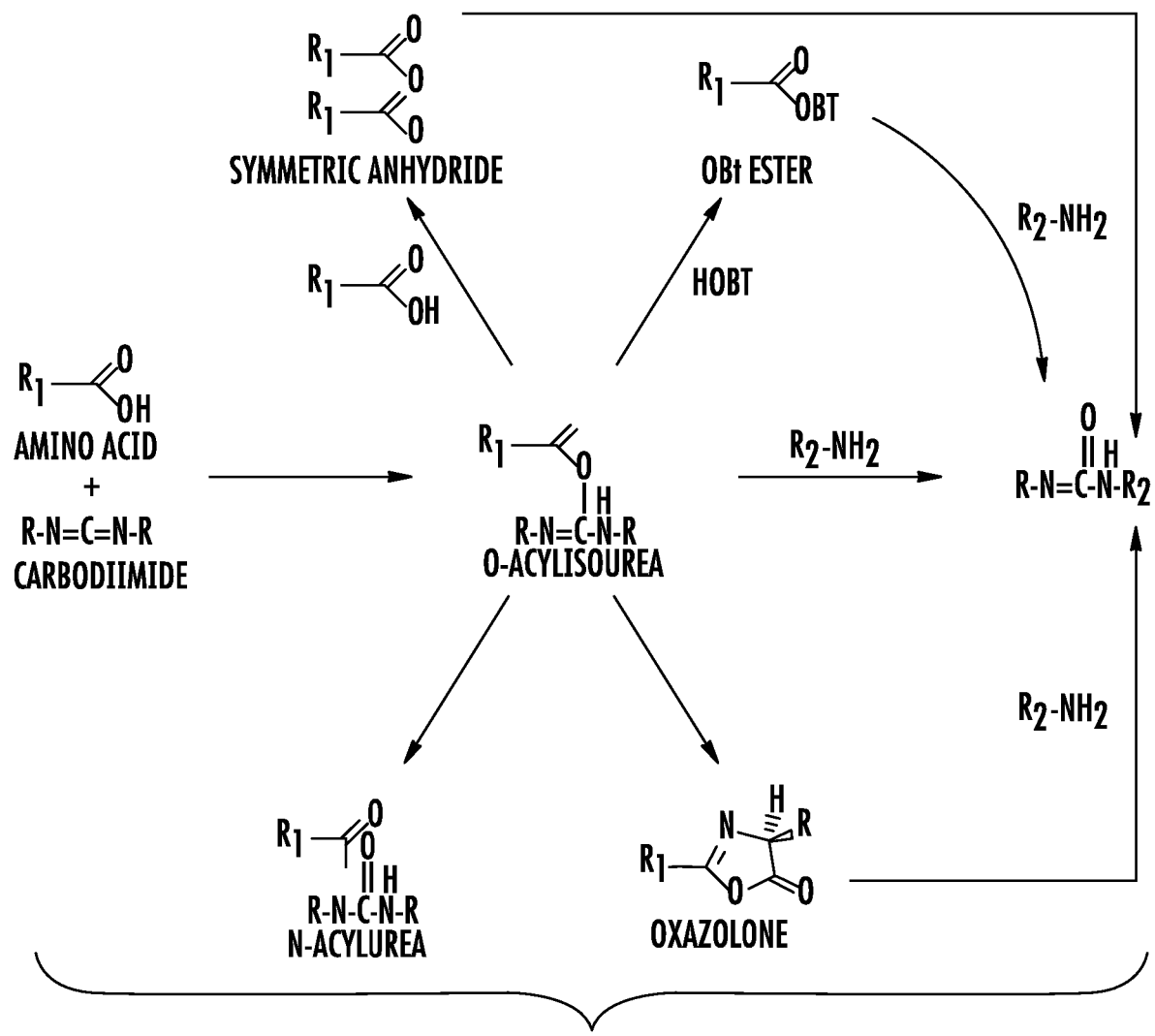
FIG. 1 is a flow diagram of Carbodiimide Based Activation.
Figure 2:
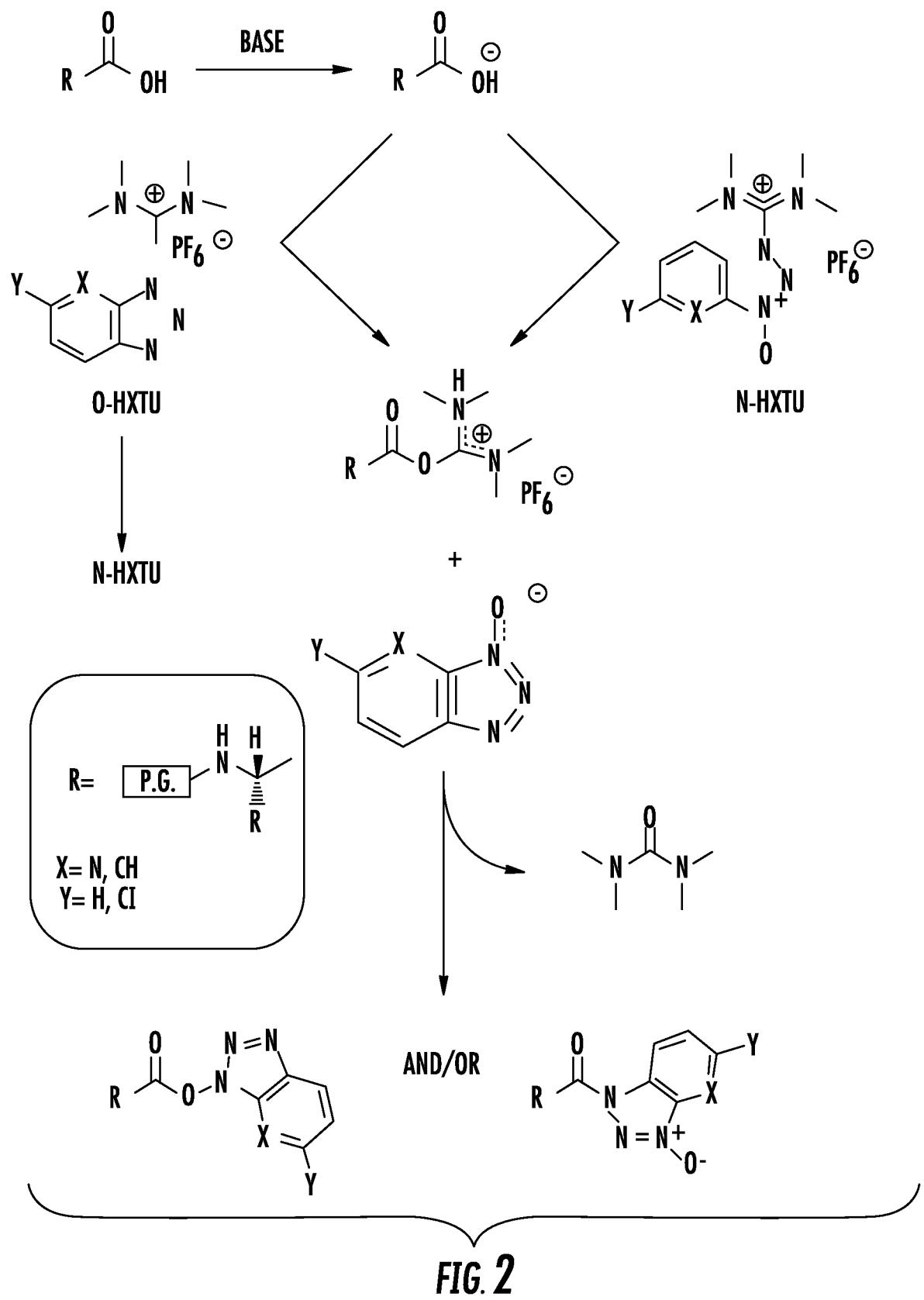
FIG. 2 is a flow diagram of Onium Salt Based Activation.

An improved carbodiimide coupling method at elevated temperatures is presented that avoids the use of a strong base while simultaneously increasing coupling efficiency. This method is based on the unexpected improvement in coupling from the use of increased amounts of carbodiimide (greater than 1 equivalent) relative to the amino acid. It was found that this combination uniquely improved coupling efficiency through more rapid formation of the o-acylisourea intermediate, avoidance of expected N-acylurea peptide formation and/or capping of the terminal amino group, and reduction in epimerization compared to the use of base with carbodiimide coupling. The efficiency of this method was verified by synthesizing three difficult peptide sequences under various conditions as shown in Tables 1-3.

The invention also applies to the synthesis of peptidomimetics; i.e., small protein-like chains designed to mimic a peptide. Because the coupling reactions described herein are for the most part identical as between peptides and peptidomimetics, the invention will be described in terms of peptides. The skilled person will, of course, understand this completely.

In a similar manner, the skilled person will understand that the term "amino acid" is used herein in its broadest sense to refer to the organic compounds that contain both amine and carboxylic acid functional groups usually along with a side chain. The skilled person is well aware of and familiar with the 22 amino acids that are naturally incorporated into polypeptides and are referred to as proteinogenic or natural amino acids. Again, because the basic coupling reactions are not limited to these particular molecules, the skilled personal will recognize that the advantages of the invention also apply to non-proteinogenic amino acids (aka "non-natural amino acids") of which 40 have been added into proteins using established synthetic steps. The results described herein use the well-established single letter designations for the amino acids in the synthesized peptides.

The basics of solid phase peptide chemistry have been well-established starting with the pioneering work of Merrifield. (R. B. Merrifield (1963) "Solid Phase Peptide Synthesis I, The Synthesis of a Tetrapeptide," J. Am. Chem. Soc. 85 (14), 2149-2154). The frequently used Fmoc (9-fluorenylmethyloxycarbonyl) protecting-group approach is well described in references that are easily available to the skilled person. (e.g., Chan and White, "Fmoc solid phase peptide synthesis, a practical approach, Oxford University Press (2000)).

The LIBERTY BLUE™ instrument referred to in the experiments is available from CEM Corporation of Matthews N.C. Relevant US patents dealing with the subject of solid phase peptide synthesis at elevated temperatures and using microwave irradiation include, but are not necessarily limited to, the following: U.S. Pat. Nos. 7,393,920; 7,550,560; 7,563,865; 7,939,628; 7,902,488; 7,582,728; 8,153,761; 8,058,393; 8,426,560; 8,846,862; 9,211,522. The contents of these are incorporated entirely herein by reference.

TABLE 1

Synthesis of Thymosin with Various Amounts of Carbodiimide

| Entry | Temp (° C.) | Coupling Time | Activation | DIEA (Equivalents) | % Purity (UPLC-MS) |
|---|---|---|---|---|---|
| 1 | 90 | 2 | DIC/Oxyma (1:1) | 0 | 63 |
| 2 | 90 | 2 | DIC/Oxyma (1:1) | 0.1 | 70 |
| 3 | 90 | 2 | DIC/Oxyma (1:1) | 0 | 75 |

Experiment Conditions:
Peptide Sequence (Thymosin)=(SEQ ID NO. 1) SDAAVDTSSEITTKDLKEKKEVVEEAEN-NH2
Synthesis Scale=0.1 mmol
Resin=Rink Amide MBHA Polystyrene Resin (0.38 mmol/g)
Instrument=Liberty Blue Microwave Peptide Synthesizer (CEM Corp., Matthews, N.C.)
Deprotection=3 mL of a 10% (w/v) piperazine in EtOH: NMP (1:9)
Microwave Deprotection Method=1 min at 90° C.
Washing=Post-Deprotection (2 mL, 2 mL, 3 mL—DMF); Post-Coupling=None
Coupling=5-fold excess of AA/DIC/Oxyma in 4 mL solution
Cleavage=5 mL of TFA/TIS/H2O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

TABLE 2

Synthesis of GRP with Various Amounts of Carbodiimide

| Entry | Temp (° C.) | Coupling Time | Activation | DIEA (Equivalents) | % Purity (UPLC-MS) |
|---|---|---|---|---|---|
| 1 | 90 | 2 | DIC/Oxyma (1:1) | 0 | 62 |
| 3 | 90 | 2 | DIC/Oxyma (2:1) | 0 | 74 |

Experiment Conditions:
Peptide Sequence (GRP)=(SEQ ID NO. 2) VPL-PAGGGTVLTKMYPRGNHWAVGHLM-NH2
Synthesis Scale=0.1 mmol
Resin=Rink Amide MBHA Polystyrene Resin (0.35 mmol/g)
Instrument=Liberty Blue Microwave Peptide Synthesizer (CEM Corp., Matthews, N.C.)
Deprotection=3 mL of a 10% (w/v) piperazine in EtOH: NMP (1:9)
Microwave Deprotection Method=1 min at 90° C.
Washing=Post-Deprotection (2 mL, 2 mL, 3 mL—DMF); Post-Coupling=None
Coupling=5-fold excess of AA/DIC/Oxyma in 4 mL solution
Cleavage=5 mL of TFA/TIS/H2O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm).

TABLE 3

Synthesis of Ubiquitin with Various Amounts of Carbodiimide

| Entry | Temp (° C.) | Coupling Time | Activation | DIEA (Equivalents) | % Purity (UPLC-MS) |
|---|---|---|---|---|---|
| 1 | 90 | 2 | DIC/Oxyma (1:1) | 0 | >68 |
| 3 | 90 | 2 | DIC/Oxyma (2:1) | 0 | >73 |

Experiment Conditions:
Peptide Sequence (Ubiquitin)=(SEQ ID NO. 3) MQIFVKTLTGKTITLEVEPSDTIENVKAKIQDKEGIPP-DQQRLIFAGKQLEDGRTLSDYNIQKESTLHLVLRL-RGG-NH2
Synthesis Scale=0.1 mmol Resin=Fmoc-PAL-PEG-PS resin (0.20 mmol/g)
Instrument=Liberty Blue Microwave Peptide Synthesizer (CEM Corp., Matthews, N.C.)
Deprotection=4 mL of a 10% (w/v) piperazine in EtOH:NMP (1:9)+0.1 M HOBt
Microwave Deprotection Method=1 min at 90° C.
Washing=Post-Deprotection (4×4 mL DMF); Post-Coupling=None
Coupling=5-fold excess of AA/DIC/Oxyma in 4 mL solution
Cleavage=5 mL of TFA/TIS/H2O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

As shown in Table 1, a significant increase in purity was observed by increasing the carbodiimide excess relative to the amino acid (75% vs. 63%). Similar improvements were observed from other peptides synthesized as shown in Tables 2 and 3. Together, these results show that not only was coupling efficiency increased, but also that potential capping from the carbodiimide was avoided. This is presumably from the increased kinetics of acylation relative the capping which thereby avoids this potential side reaction. Additionally, the increased temperature of the coupling reaction is also helpful for ensuring the urea formed from the carbodiimide is fully soluble and removed during subsequent draining and washing steps. Therefore, elevated temperatures provide protection against potential solubility issues from larger amounts of urea generated through the use of greater than 1 equivalent of carbodiimide.

The epimerization of each amino acid was then investigated through hydrolysis, subsequent derivatization, and analysis by gas chromatography (CAT GmbH). We observed extremely low levels of epimerization using the excess carbodiimide method. This is presumably because the coupling reaction is completed the fastest (short lifetime for activated species) and no external base is present. Therefore, this method offers advantages over any previous method described for coupling at elevated temperatures to date.

TABLE 4

Epimerization Analysis of the Synthesis of Thymosin with 2-Equivalents of Carbodiimide Alanine 0.14% D-Enantiomer
Valine 0.10% D-Enantiomer
Threonine >99.7% L-Threonine
<0.10% D-Threonine
<0.10% L-allo Threonine
<0.10% D-allo Threonine
Isoleucine >99.7% L-Isoleucine
<0.10% D-Isoleucine
<0.10% L-allo-Isoleucine
<0.10% D-allo-Isoleucine
Leucine 0.12% D-Enantiomer
Serine 0.11% D-Enantiomer
Aspartic acid 0.10% D-Enantiomer
Glutamic acid 0.22% D-Enantiomer
Lysine <0.10% D-Enantiomer The use of bases during the coupling process is not ideal as they can lead to undesirable side reactions. Collins et al. showed how cysteine epimerization was minimal at 90° C. under a carbodiimide based coupling method without the presence of any base. (J. Collins et al., "High-Efficiency Solid Phase Peptide Synthesis (HE-SPPS)," Org. Lett., vol. 16, pp. 940-943, 2014). Palasek et al. had shown how significant cysteine epimerization can occur under onium salt activation methods with the presence of DIEA and NMM present at 2 equivalents. (S. Palasek, Z. Cox et al., "Limiting racemization and aspartimide formation in microwave-enhanced Fmoc solid phase peptide synthesis," J. Pept. Sci., vol. 13, pp. 143-148, 2007). It is also known that the Fmoc protecting group is slowly labile to DIEA. This can be increased at higher temperatures and leads to undesirable insertion sequences which can be difficult to separate.

TABLE 5

Comparison of Carbodiimide and Onium Salt Activation Strategies for Peptide Coupling at Elevated Temperature

| Feature | NEW METHOD DIC/Oxyma (>1:1) | STANDARD CARBODIIMIDE DIC/Oxyma (1:1) | ONIUM SALTS [Aminium] HBTU/DIEA (0.9:2) | ONIUM SALTS [Phosphonium] PyBOP/DIEA (1:2) |
|---|---|---|---|---|
| Coupling Time Required | FASTEST | FAST | LONGER - Temperature limited | LONGER - Temperature limited |
| Synthesis Purity | HIGHEST | HIGH | MODERATE | MODERATE |
| Pre-activation required | NO | NO | NO* (w/slight deficit) | NO |
| Stability of activated ester formed | BEST | BEST | LIMITED | LIMITED |
| Epimerization of Cysteine derivatives | OK | OK | BAD | BAD |
| δ-lactam formation of Arginine | OK | OK | BAD | BAD |
| Stability of hyper-acid sensitive resins | YES | LIMITED | YES | YES |

TABLE 5-continued

Comparison of Carbodiimide and Onium Salt Activation Strategies for Peptide Coupling at Elevated Temperature

| Feature | NEW METHOD DIC/Oxyma (>1:1) | STANDARD CARBODIIMIDE DIC/Oxyma (1:1) | ONIUM SALTS [Aminium] HBTU/DIEA (0.9:2) | ONIUM SALTS [Phosphonium] PyBOP/DIEA (1:2) |
|---|---|---|---|---|
| Stability of activator reagents in solution | GOOD | GOOD | LESS STABLE | LESS STABLE |

TABLE 6

Comparison of Carbodiimide Activation Strategies for Peptide Coupling at Elevated Temperature

| Feature | NEW METHOD DIC/Oxyma (1:1) | NEW METHOD DIC/Oxyma/DIEA (1:1:0.1) | STANDARD CARBODIIMIDE DIC/Oxyma (1:1) |
|---|---|---|---|
| Formation of O-acylisourea | FASTEST | SLIGHTLY REDUCED | OK |
| Synthesis Purity | HIGHEST | HIGHER | HIGH |
| Pre-activation required | NO | NO | NO |
| Stability of activated ester formed | BEST | GOOD | BEST |
| Epimerization of Cysteine derivatives | BEST | OK | BEST |
| δ-lactam formation of Arginine | BEST | OK | BEST |
| Stability of hyper-acid sensitive resins | OK | YES | NO |
| Stability of activator reagents in solution | GOOD | GOOD | GOOD |

In the specification there has been set forth a preferred embodiment of the invention, and although specific terms have been employed, they are used in a generic and descriptive sense only and not for purposes of limitation, the scope of the invention being defined in the claims.

The invention claimed is:

1. In a method of coupling initially Fmoc-protected amino acids into peptides or peptidomimetics, the improvement comprising:
   carrying out activation and coupling in the same vessel;
   incorporating a carbodiimide in an amount between 1.5 and 4 equivalents as compared to the amino acid to be activated, wherein the amino acid is initially Fmoc-protected;
   in the presence of an activator additive; and
   at a temperature greater than 70° C.

2. A method according to claim 1 in which the activated amino acid is coupled to at least one other amino acid that is linked to a solid phase resin.

3. A method according to claim 1 limited to a total coupling time less than 10 minutes.

4. A method according to claim 1 limited to a total coupling time less than 15 minutes.

5. A method according to claim 1 wherein the activator additive is present in an amount between 1 and 1.5 equivalents compared to the amino acid to be activated.

* * * * *